United States Patent
Smith

(10) Patent No.: US 8,939,964 B2
(45) Date of Patent: Jan. 27, 2015

(54) ELECTRICALLY SWITCHABLE MULTI-SPOT LASER PROBE

(75) Inventor: Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 338 days.

(21) Appl. No.: 13/308,875

(22) Filed: Dec. 1, 2011

(65) Prior Publication Data
US 2013/0141672 A1 Jun. 6, 2013

(51) Int. Cl.
*A61B 18/20* (2006.01)

(52) U.S. Cl.
USPC .................................. 606/2; 606/17; 606/18

(58) Field of Classification Search
USPC ...................................................... 606/2–19
See application file for complete search history.

(56) References Cited

U.S. PATENT DOCUMENTS

| | | | |
|---|---|---|---|
| 5,151,814 A | 9/1992 | Grinberg et al. | |
| 5,233,673 A | 8/1993 | Vali et al. | |
| 6,031,658 A | 2/2000 | Riza | |
| 6,129,721 A | 10/2000 | Kataoka et al. | |
| 7,473,249 B2 | 1/2009 | Scheller et al. | |
| 7,566,173 B2 | 7/2009 | Auld et al. | |
| 8,357,312 B2 | 1/2013 | Sun | |
| 2007/0265602 A1 | 11/2007 | Mordaunt et al. | |
| 2009/0015923 A1 | 1/2009 | Auld et al. | |
| 2011/0144627 A1 | 6/2011 | Smith | |

FOREIGN PATENT DOCUMENTS

| | | |
|---|---|---|
| WO | 0219018 A1 | 3/2002 |
| WO | 2009/009246 A1 | 1/2009 |

OTHER PUBLICATIONS

Bibliographic Data Only: "Functionally Graded Material Tube and Method for Use of the Same in Implantation"; currently pending unpublished; U.S. Appl. No. 13/488,816, filed Jun. 5, 2012.

*Primary Examiner* — Aaron Roane

(57) ABSTRACT

In certain embodiments, a system may include a housing, one or more lenses, and a scanning system. The housing has an interior region. A lens is disposed within the interior region and transmits a light beam. The scanning system is disposed within the interior region and comprises a number of scanning cells, where each scanning cell comprises an electro-optical (EO) material. The scanning system performs the following for a number of iterations to yield a spot pattern: receive one or more voltages and electrically steer the light beam with the EO material from a current direction to a next direction in response to the voltages.

13 Claims, 6 Drawing Sheets

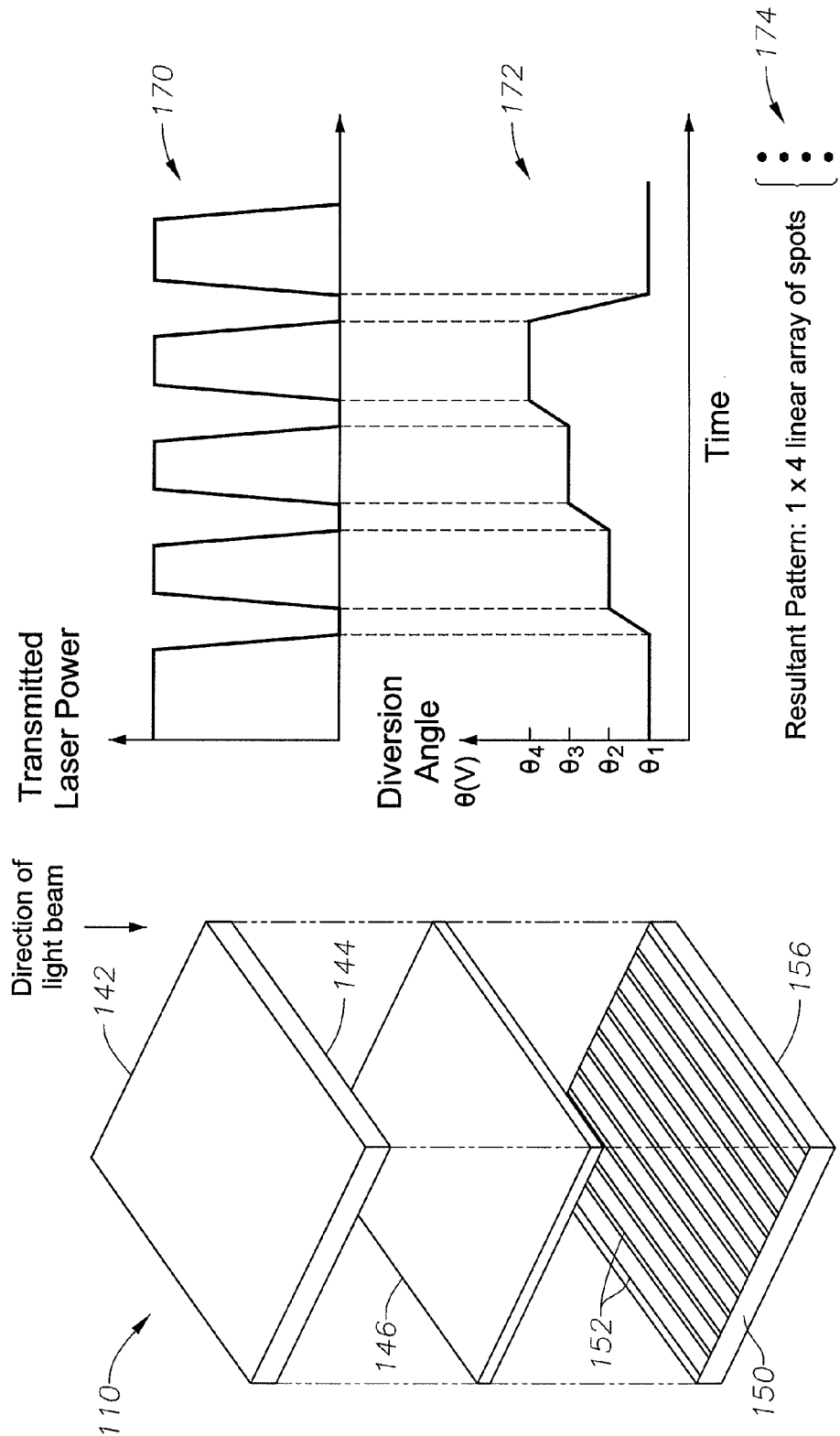

ELECTRICALLY SWITCHABLE MULTI-SPOT LASER PROBE

TECHNICAL FIELD

The present disclosure relates generally to laser probes, and more particularly to an electrically switchable multi-spot laser probe.

BACKGROUND

Laser probes may be used for a variety of different purposes. In laser photocoagulation, a laser probe may be used to cauterize blood vessels at laser burn spots across the retina. Certain types of laser probes burn multiple spots at a time, which may result in faster and more efficient photocoagulation. Some of these multi-spot laser probes split a single laser beam into multiple laser beams that have a laser spot pattern and deliver the beams to an array of optical fibers that have a corresponding fiber pattern. The optical fibers transmit the beams to yield a spot pattern at the target. In certain situations, however, these laser probes are not as efficient as desired.

BRIEF SUMMARY

In certain embodiments, a system may include a housing, one or more lenses, and a scanning system. The housing has an interior region. A lens is disposed within the interior region and transmits a light beam. The scanning system is disposed within the interior region and comprises a number of scanning cells, where each scanning cell comprises an electro-optical (EO) material. The scanning system performs the following for a number of iterations to yield a spot pattern: receive one or more voltages and electrically steer the light beam with the EO material from a current direction to a next direction in response to the voltages.

In certain embodiments, a method may include transmitting a light beam through one or more lenses disposed within an interior region of a housing. One or more voltages are received by a scanning system disposed within the interior region. The scanning system has scanning cells, including a first scanning cell and a second scanning cell, where the first scanning cell is orthogonal to the second scanning cell, and each scanning cell comprises an electro-optical (EO) material. The following is performed by the scanning system for a number of iterations to yield a laser spot pattern at a number of optical fibers: receiving one or more voltages and electrically steering the light beam with the EO material from a current direction to a next direction in response to the one or more voltages.

BRIEF DESCRIPTION OF THE DRAWINGS

Exemplary embodiments of the present disclosure will now be described by way of example in greater detail with reference to the attached figures, in which:

FIGS. 3 and 4 illustrate a scanning cell of a probe system according to certain embodiments;

FIG. 6 illustrates an example of a pattern of diversion angles that may yield a one-dimensional spot pattern according to certain embodiments;

DETAILED DESCRIPTION OF EXAMPLE EMBODIMENTS

Figure 1:
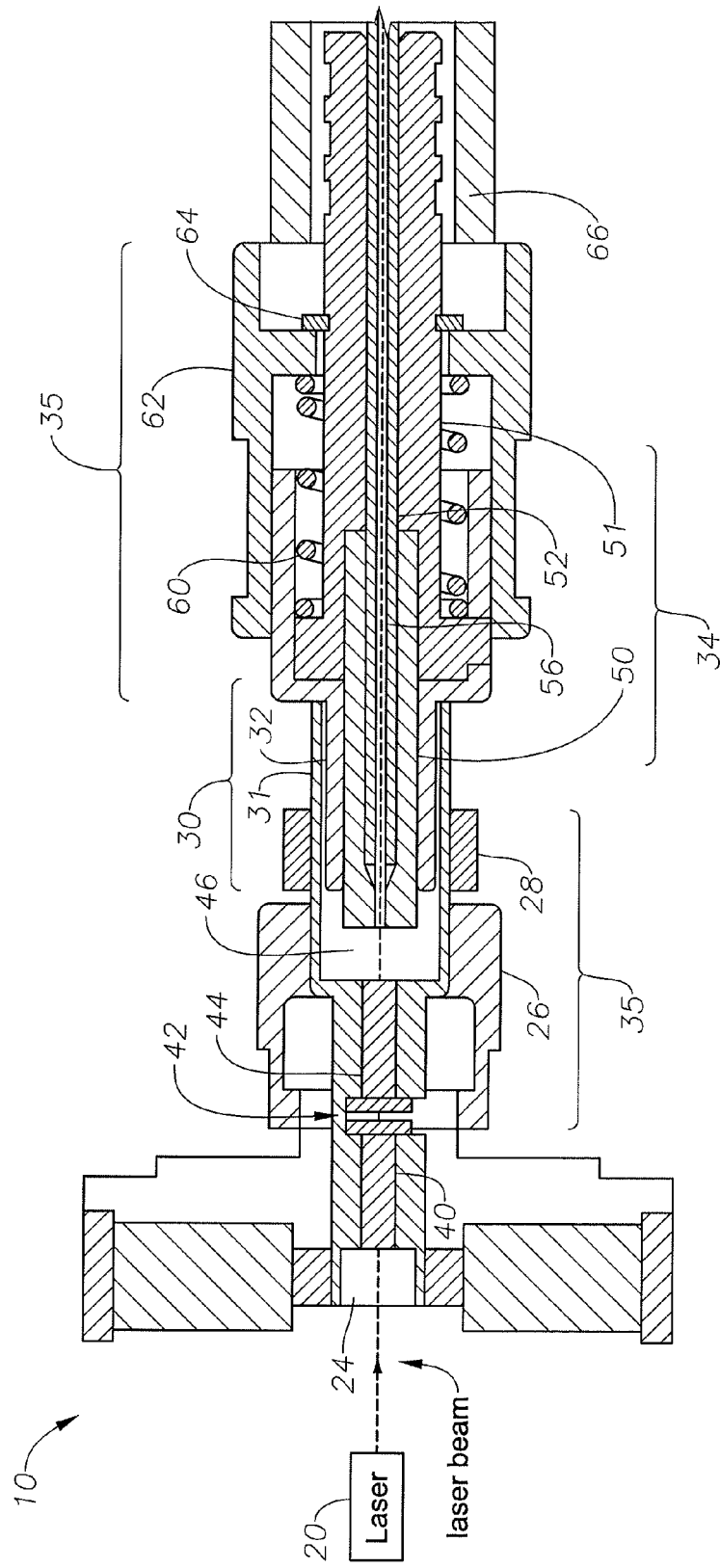
FIG. 1 illustrates an example of an electrically switchable multi-spot laser probe system according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIG. 1 illustrates an example of an electrically switchable multi-spot laser probe system 10 according to certain embodiments. In the illustrated example, system 10 includes a laser 20, a laser port 24, an adapter 30, an optical fiber connector 34, a strain relief 66, and coupling devices 35 coupled as illustrated. Adapter 30 includes proximal adapter 31 and distal adapter 32. Disposed within adapter 30 are a lens 40, a scanning system 42, and a lens 44. Optical fiber connector 34 may include a ferrule 50 coupled to a connector body 51. A cylindrical insert 52 may be disposed within optical fiber connector 34, and a bundle of optical fibers 56 may be disposed within cylindrical insert 52. Adapter 30, lens 44, and optical fiber connector 34 may form an air gap 46. Coupling devices 35 include a threaded cylinder 26, a retaining ring 28, a spring 60, a coupling nut 62, and a C-clip 64.

In an example of operation, laser 20 emits a laser beam that is focused towards lens 40, which collimates the laser beam. Scanning system 42 and a controller (not shown) scan and switch the beam on and off (on/off) to yield a laser spot pattern that matches a fiber pattern of the bundle of optical fibers 56. Lens 44 refocuses the beam onto optical fibers 56. Optical fibers 56 transmit the beam through any suitable device, for example, a laser probe. The beam may travel through the laser probe to any suitable target, such as the posterior region of an eye, such as a human eye. The beam forms a pattern at the target that matches the laser spot and fiber patterns. The beam may be used for any suitable purpose, such as for performing photocoagulation on the retina of the eye.

In certain embodiments, laser 20 may be any suitable light source that can generate a laser beam. Laser 20 may have a laser shutter that can switch the beam on/off. Laser port 24 may be any suitable structure that supports certain components of system 10 such that laser 20 can direct a laser beam towards lens 40.

Adapter 30 is an example of a housing with a substantially cylindrical shape and a substantially cylindrical interior region. The interior region may have any suitable size and shape to house lenses 40 and 44 and scanning system 42. Adapter 30 may have any suitable size, e.g., a length between 1 to 3 centimeters (cm) and an inner diameter between 200 to 300 micrometers (μm). Adapter 30 may comprise any suitable material, such as a metal.

A lens 40 may be any suitable lens that can collimate a laser beam. For example, lens 40 may be a gradient index (GRIN)

lens. Scanning system 42 directs the laser beam in different directions, or scans the beam. A controller (not shown) instructs scanning system 42 to scan and laser 20 to switch the beam on/off in a coordinated manner to yield a laser spot beam. Scanning system 42 may include scanning cells that comprise an electro-optical (EO) material that changes its refractive index in response to an applied electrical field. An example of an EO material is described in more detail later with reference to FIGS. 2A and 2B. Accordingly, scanning system 42 may change the direction of a light beam in response to an applied voltage. Scanning system 42 is described in more detail later with reference to FIGS. 3 through 5. Lens 44 may be any suitable lens that can refocus a multi-spot beam onto the focal plane defined by the proximal end faces of fibers 56. For example, lens 44 may be a GRIN lens.

Optical fiber connector 34 couples optical fibers 56 to adapter 30 to allow optical fibers 56 to receive the laser beam from adaptor 30. Optical fibers 56 may be arranged at an aperture of optical fiber connector 34 such that the ends of fibers 56 form a fiber pattern that matches the laser spot pattern. A laser spot pattern matches a fiber pattern if each beam spot hits or substantially hits an optical fiber 56 to allow fibers 56 to optimally receive the beam. Any suitable beam spot and fiber patterns may be used. Examples of laser spot patterns are described with reference to FIGS. 6 through 8.

Connector body 51 couples optical fiber connector 34 to adapter 30 and/or devices connected to a probe. Connector body 51 may have any suitable shape, e.g., a cylindrical shape within which optical fibers 56 may be disposed. An optical fiber 56 is an optical waveguide that can transmit light. An optical fiber 56 has a transparent core surrounded by a transparent cladding. Optical fiber 56 may comprise any suitable transparent material, e.g., glass. Optical fiber 56 may have any suitable size. For example, core 65 may have a diameter in the range of 50 to 100 µm, such as approximately 75 µm, and cladding may have an outer diameter in the range of 80 to 150 µm, such as, 90 µm.

Coupling devices 35 couple together certain components of system 10. For example, threaded cylinder 26 and retaining ring 28 couple together adapter 30 and laser port 24. Spring 60, coupling nut 62, and C-clip 64 couple together optical fiber connector 34 and adaptor 30.

Figure 2A:
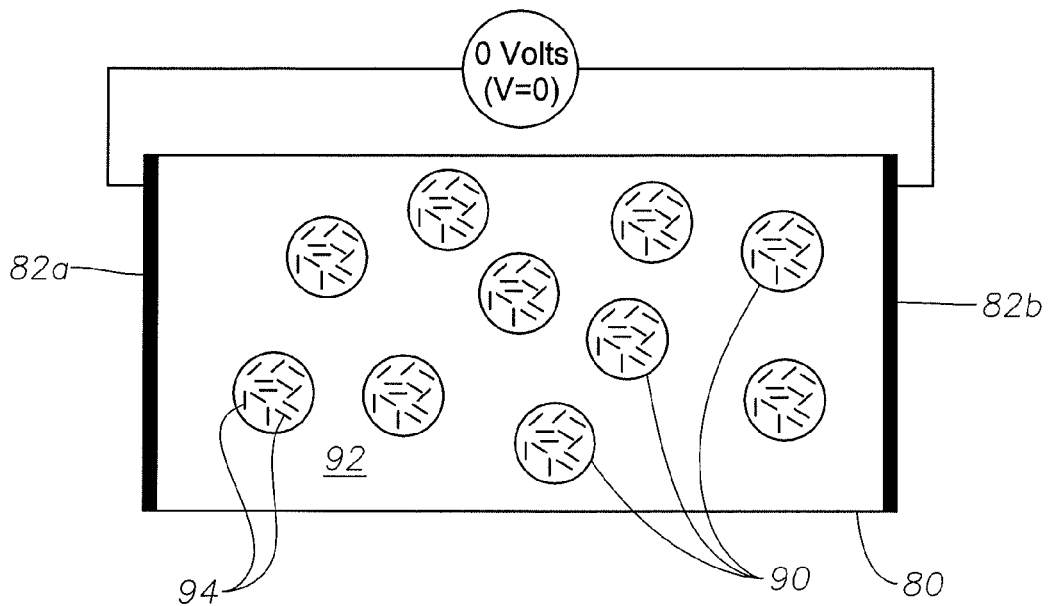
FIGS. 2A and 2B illustrate an example of an electro-optical (EO) material according to certain embodiments.
Figure 2B:
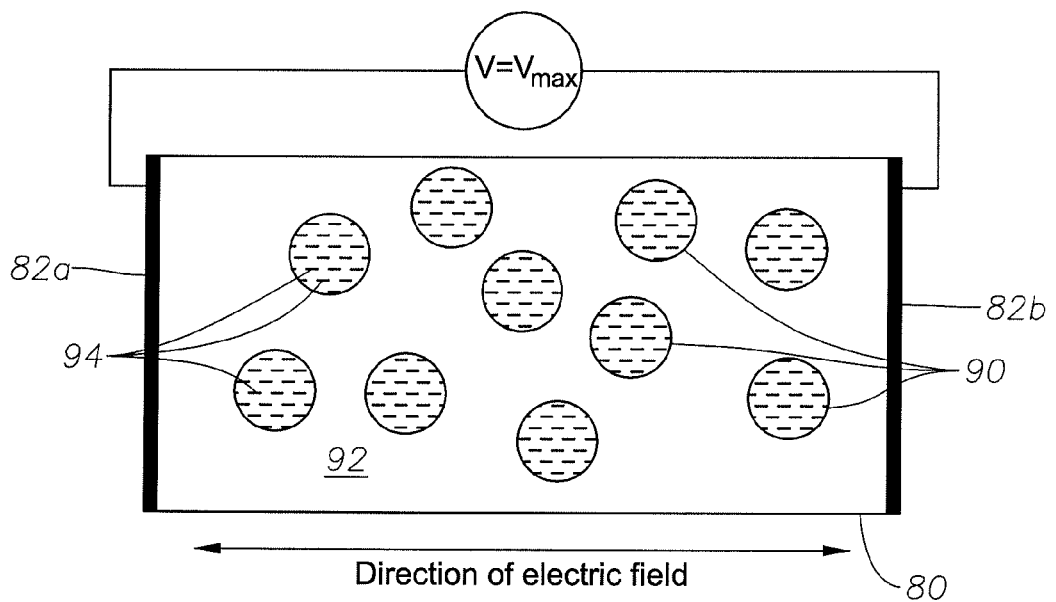

FIGS. 2A and 2B illustrate an example of an electro-optical (EO) material according to certain embodiments. In the example, EO material 80 is disposed between electrodes 82 (82a-b). EO material 80 may be a liquid crystal (LC) material such as a polymer-dispersed liquid crystal (PDLC) material. In PDLC material, tiny circular or quasi-circular LC droplets 90 with LC molecules 94 are immersed within a medium of hardened polymer 92. Droplets 90 are immobilized within polymer 92, but LC molecules 94 within droplets 90 are free to rotate. In the absence of an electric field, the orientations of LC molecules 94 tend to be random, and the resulting effective refractive index of LC droplet 90 is $n_{LC}(V=0)=n_{LCo}$ (FIG. 2A).

As increasing voltage is applied to the PDLC material, LC molecules 94 tend to orient more and more along the direction of the electric field, and the refractive index of droplet 90 changes from $n_{LCo}$ to $n_{LC}(V)$. At maximum voltage $V_{max}$, LC molecules 94 have aligned with the electric field, and the refractive index of LC droplet 90 is $n_{LC}(V_{max})$ (FIG. 2B).

LC droplets 90 may be on the order of a wavelength of laser light or smaller to avoid scattering light from the incident beam off LC droplets 90. The PDLC material illuminated by the laser beam appears as an effective medium with an effective refractive index $n_{eff}$, which is dependent on the constant polymer refractive index $n_{polymer}$ and the voltage-dependent LC droplet effective refractive index $n_{LC}$. Therefore, the effective index $n_{eff}$ is also voltage-dependent and varies from $n_{effo}$ at 0 volts to $n_{eff-max}$ at $V_{max}$.

Figure 3:
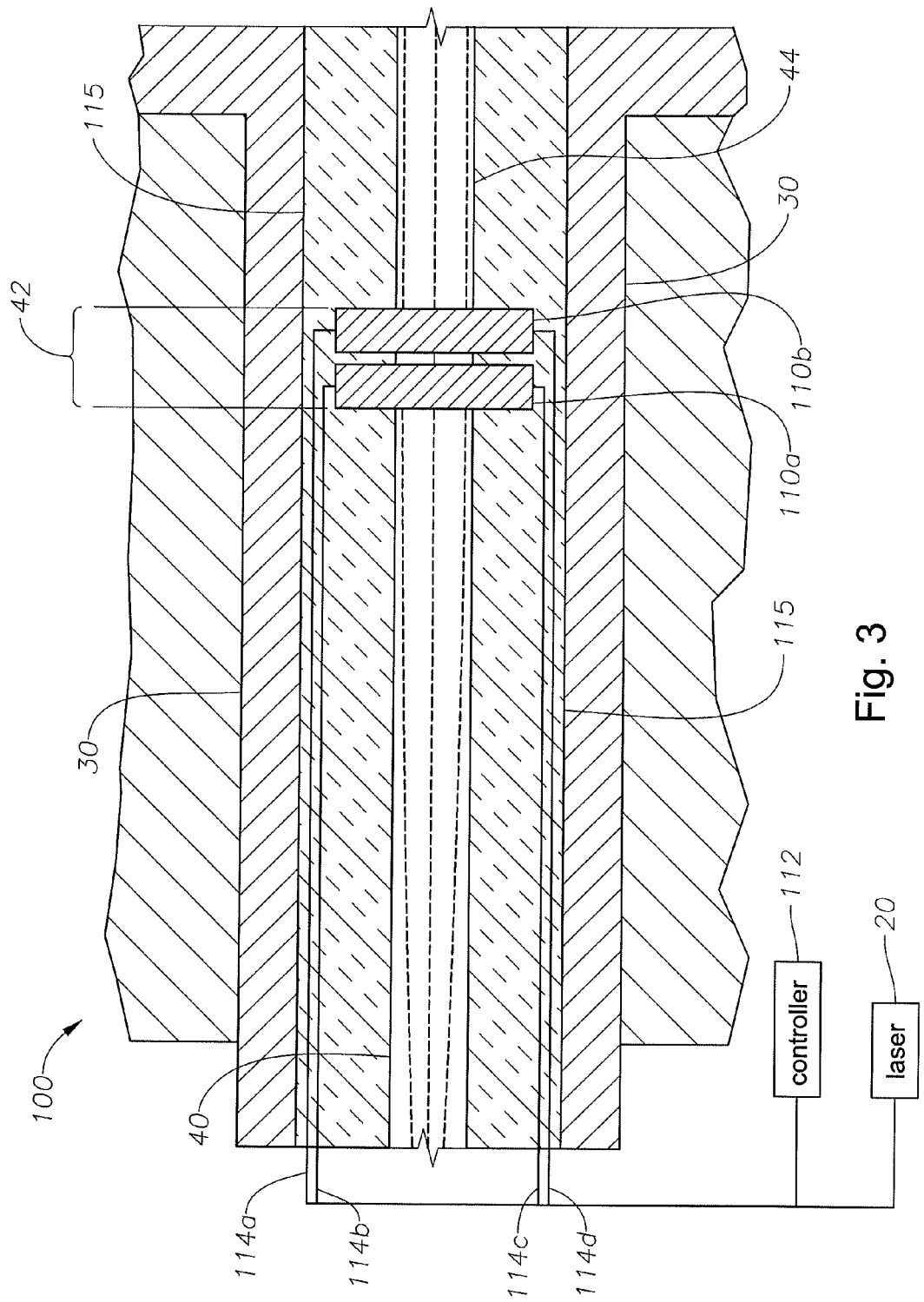

FIG. 3 illustrates a system 100 within probe system 10, and FIG. 4 illustrates a scanning cell 110 of system 100. In the illustrated example, system 100 is coupled to a controller 112 and laser 20. System 100 includes a housing (such as adapter 30), one or more lenses 40 and/or 44, a scanning system 42, and electrodes 114 (114a-d) coupled as shown. Electrodes 114 are disposed within the housing. In certain embodiments, electrodes 114 may be disposed within an inner cylinder 115 that is disposed within the housing. Inner cylinder 115 electrically insulates electrodes 114 and may comprise any suitable material, e.g., ceramic.

Scanning system 42 comprises one or more scanning cells 110 (110a-b), where each scanning cell 110 comprises an electro-optical (EO) material. Scanning system 42 performs the following to yield a spot pattern: receive one or more voltages and electrically steer the light beam with the EO material from a current direction to a next direction in response to the voltages. The beam may be steered to a diversion angle θ with respect to a cylindrical axis of the housing. Diversion angle θ may have any suitable value, such as a value in the range of 0 to 90 degrees.

Controller 112 steers light by applying different voltages across different portions of scanning cell 110. In the example, scanning cell 110 includes cover plate 142, electrode layer 144 disposed outwardly from cover plate 142, OE element 146 disposed outwardly from electrode layer 144, electrode layer 150 (with strip electrodes 152) disposed outwardly from OE element 146, and a cover plate 156.

Cover plates 142 and 156 may comprise any suitable transparent material, such as glass, and may have any suitable shape and size, such as a flat planar shape with a thickness in the range of 10 to 200 microns. Electrode layers 144 and 150 apply different voltages across OE element 146. Electrode layers 144 may comprise any suitable conductive material, such as indium tin oxide (ITO). In certain embodiments, electrode layer 150 comprises strip electrodes 152, where at least two strip electrodes 152 apply different voltages. A strip electrode 152 may comprise any conductive material, such as ITO. In certain embodiments, strip electrodes 152 are individually addressable to yield a monotonically changing voltage vs. position pattern.

EO element 46 changes its refractive index in response to an applied electrical field. Accordingly, EO element 46 may change the direction of a light beam in response to an applied voltage. EO element 46 may comprise any suitable EO material, such as an optically transparent electrically conductive (OTEC) material.

Controller 112 applies voltage to scanning cell 110 to steer a laser beam. In certain embodiments, controller 112 may change the voltages to change the direction of a light beam to yield the laser spot pattern. Controller 112 may also send instructions to laser 20 to switch on when the beam is directed to a location where a spot should be and to switch off when the beam is not pointed at a spot location (for example, when the beam is moving from one spot location to another spot location).

One spot may be formed at each spot location of a spot pattern during a scan cycle. (In certain cases, a spot location may be visited more than once during a scan cycle.) The scan cycles may occur at any suitable rate. In certain embodiments, the scan rate may be determined with respect to a burn time. In some cases, the scan rate may be selected such that multiple scan cycles (such as 2, 3, 4, or more cycles) occur during the burn time. For example, if the burn time is 200 milliseconds (ms), then the scan cycle may be 50 ms.

Controller 112 may form any suitable laser spot patterns of one or more spots. For example, an m×n pattern has m rows and n columns, where m=n or m>n, and m, n=1, 2, 3, .... As another example, a cross pattern has rows of spots radiating from a center point, which may or may not have a spot. Examples of laser spot patterns are described in more detail with reference to FIGS. 6 through 8. Moreover, a user may instruct controller 112 to form a different pattern in real time.

In certain embodiments, system 100 includes a scanning cell 110 that steers a beam in one dimension to yield a one-dimensional spot pattern. In other embodiments, system 100 includes two scanning cells 110 that steer a beam in two dimensions to yield a two-dimensional spot pattern. In these embodiments, two or more scanning cells 110 (110a-b) may be positioned in different directions to steer a light beam in two dimensions. For example, two scanning cells 110 may be position orthogonally such that cell 110a moves the beam along a first coordinate axis and cell 110b moves the beam along a second coordinate axis orthogonal to the first coordinate axis to allow for two-dimensional beam steering.

FIGS. 5A through 5D illustrate an example of voltages applied to a scanning cell 110 according to certain embodiments. The figures show how voltages may be applied to scanning cell 110 to yield a monotonically changing refractive index versus position pattern.

Figure 5A:
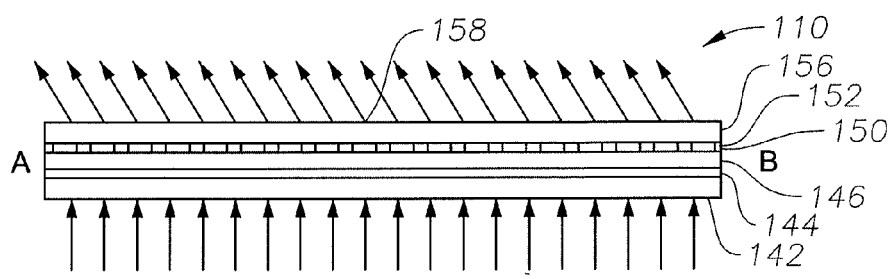
FIGS. 5A through 5D illustrate an example of voltages applied to a scanning cell according to certain embodiments.
Figure 5B:
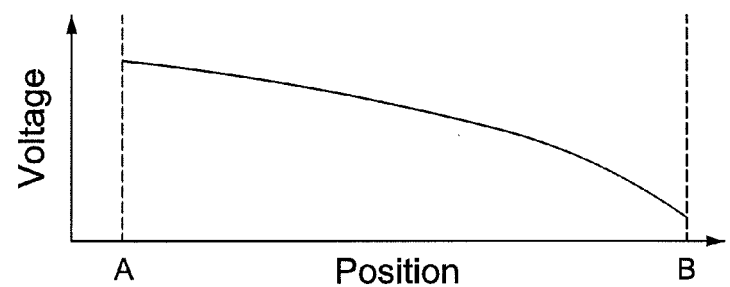
Figure 5C:
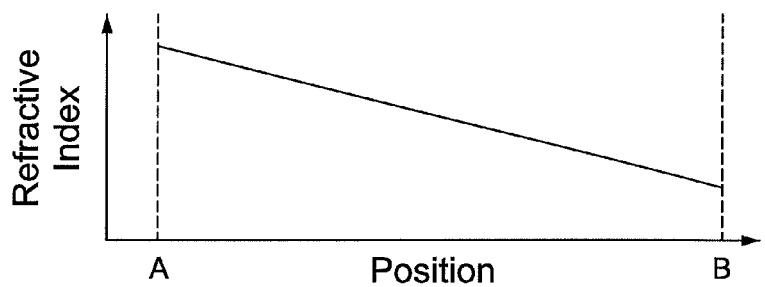
Figure 5D:
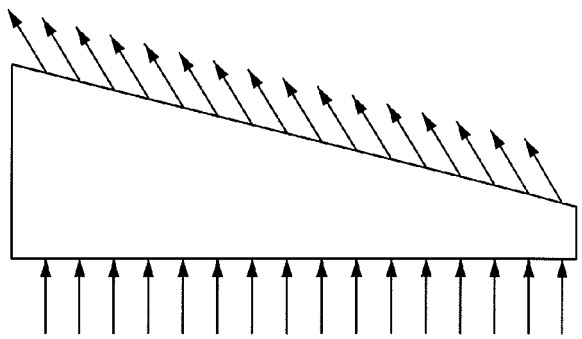

FIG. 5A illustrates an example of a scanning cell 110 with strip electrodes 152 and sides A and B. Different strip electrodes 152 may apply different voltages to yield a voltage vs. position pattern. Any suitable voltages may be applied. In the example of FIG. 5B, the voltages monotonically change with respect to position from side A to side B, e.g., from a voltage in a range of 10 to 250 volts at side A to a voltage in a range of 0 to 5 volts at side B. The voltage vs. position pattern yields a refractive index vs. position pattern. In the example of FIG. 5C, the refractive index monotonically changes with respect to position from side A to side B, e.g., from a refractive index in a range of 1.5 to 1.8 at side A to a refractive index in a range of 1.4 to 1.6 at side B. Accordingly, scanning cell 110 may operate similarly to a wedge-shaped prism of FIG. 5D.

The time for a beam to pass through an optical element is inversely dependent on its optical thickness, which is product of the refractive index and thickness of cell 110 where the beam is traveling. In the illustrated example, the cell thickness is constant across the entire cell 110 and the refractive index varies across cell 110, so the optical thickness, and thus the beam transit time, varies monotonically across the cell. The refractive index is lower on the B side of the cell than the A side, so the beam passes through the B side of the cell faster than on the A side.

In certain situations, incident and emitted beams are collimated. When a collimated beam is normally incident on cell 110 of FIG. 5A, the beam reaches an outer surface 158 of plate 156 on the B side more quickly than it does on the A side because the reflective index is lower on the B side than on the A side. According to optical principles, the beam emerging from surface 158 should be planar, with the wavefront perpendicular to the beam direction. Thus, there is beam steering to the A side as the beam exits cell 140. Accordingly, rays between the planar wave front incident on the cell and the planar wave front exiting the cell have the same total optical path length. The same principle applies for the wedge prism, except in that case, the refractive index is constant and the prism thickness varies with lateral position. But the end result is the same: the planar striped LC cell has the same effect on incident light as a constant-index wedge prism.

FIG. 6 illustrates an example of a pattern of diversion angles that may be used to yield a one-dimensional laser spot pattern. In certain embodiments, the voltage applied to scanning cell 110 may be changed to change diversion angle θ. In the example, graph 172 shows diversion angle changing with respect to time from $θ_i=θ_1$ to $θ_4$. The changes in diversion angle θ may yield a particular pattern of emitted light. In certain embodiments, the laser power may be synchronized to be on when diversion angle θ is at a desired angle $θ_i$, but off when diversion angle θ transitioning between desired angles $θ_i$. The resulting light pattern may have clearer, less blurry, spots. In the example, graph 174 shows the pattern of emitted light resulting from the synchronized changes in diversion angle θ and the transmitted laser power.

Figure 7:
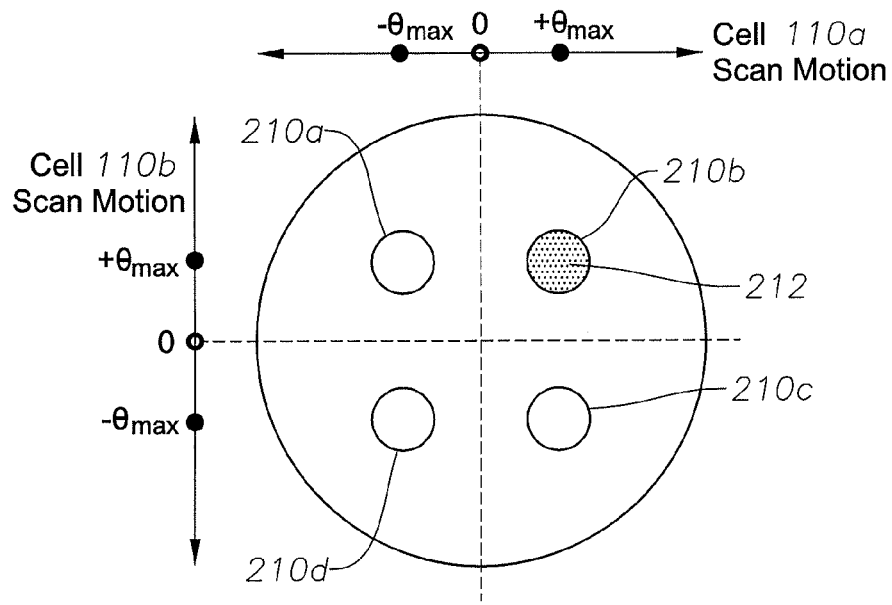
FIG. 7 illustrates an example of a 2×2 spot pattern that may be formed by scanning cells according to certain embodiments.

FIG. 7 illustrates an example of an m×n=2×2 spot pattern that may be formed by scanning cells 110 (110a-b). In the example, the scan angle of a laser beam from a scanning cell 110 is between $+θ_{max}$ and $-θ_{max}$. Controller 112 controls cells 110 and laser 20 so that the beam jumps rapidly between spot locations 210 (a-d), but remains at each spot location 210 for a dwell time to yield a beam spot 212. In certain embodiments, controller 112 may stop the beam when the scanning system is changing directions, and start the beam when the scanning system is at a fixed position. "Stopping the beam" may refer to any action that stops the beam, such as blocking or turning off the beam. "Starting the beam" may refer to any action that starts the beam, such as unblocking or turning on the beam. Controller 112 may perform these actions by instructing laser 20 to perform these actions.

The beam may visit spot locations 210 in any suitable order. For example, the beam may jump between spot locations 210a and 210b, remain at spot location 210b for a dwell time, jump between spot locations 210b and 210c, remains at spot location 210c for a dwell time, etc. The resulting pattern is a 2×2 square array that may be directed to fibers with a similar 2×2 proximal fiber pattern. The beam travels through the fibers and through a distal fiber pattern to create a beam pattern (which typically matches the distal fiber pattern) on the target, such as a retina. The distal fiber pattern may be any suitable pattern, e.g., a pattern of p=m×n spots, such as a 2×2 pattern or a 1×4 pattern.

Figure 8:
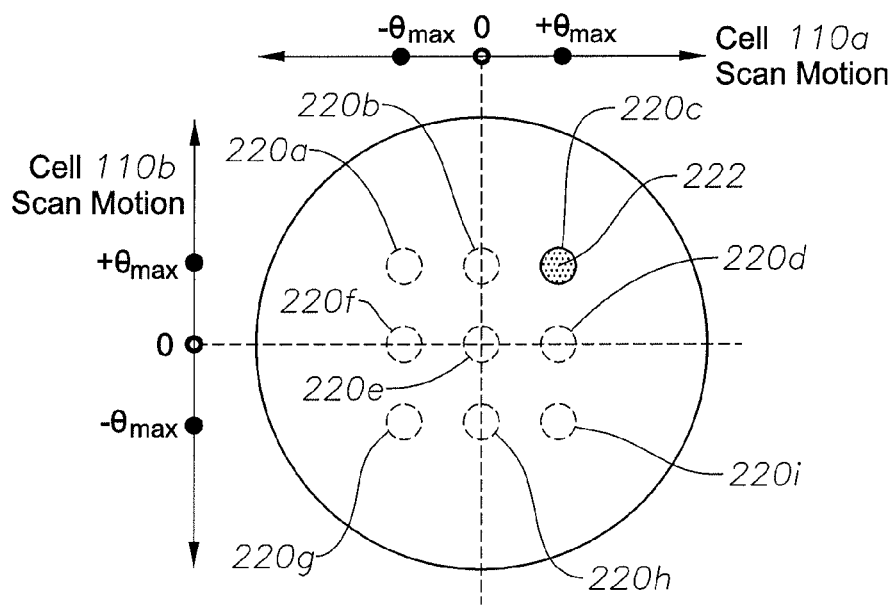
FIG. 8 illustrates an example of a 3×3 spot pattern that may be formed by scanning cells according to certain embodiments.

FIG. 8 illustrates an example of an m×n=3×3 spot pattern that may be formed by scanning cells 110 (110a-b). Controller 112 controls cells 110 and laser 20 so that the beam jumps rapidly between spot locations 220 (a-d), but remains at each spot location 220 for a dwell time to yield beam spot 222. The beam may visit spot locations 220 in any suitable order. For example, the spot locations may be visited in the order 220a, 220b, 220c, ... , 220i. The resulting pattern is a 3×3 square array that may be directed to fibers with a similar 3×3 proximal fiber pattern and then travel through the fibers to a distal fiber pattern. The distal fiber pattern may be any suitable pattern, such as a 3×3 pattern or a 1×9 pattern.

Any suitable dwell time may be used. In certain embodiments, the dwell time may be selected with respect to the scan time and number of spots in the scan patter. For example, if the scan time for a four-spot pattern is 40 ms, the dwell time may be approximately 10 ms. In certain embodiments, controller 112 may be configured to use different dwell times for different situations and for different spot locations of the same pattern. For example, certain spots of a pattern that travel farther to the target may be larger, so they may have less irradiance than the spots that do not travel as far. Thus, these spots may have a longer dwell time to compensate for the reduced irradiance.

A component (such as controller 112) of the systems and apparatuses disclosed herein may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A system comprising:
a housing having an interior region;
one or more lenses disposed within the interior region, each lens configured to transmit a light beam; and
a scanning system disposed within the interior region, the scanning system comprising a plurality of scanning cells comprising a first scanning cell and a second scanning cell, the first scanning cell orthogonal to the second scanning cell, each scanning cell comprising an electro-optical (EO) material, the scanning system configured to perform the following for a number of iterations to yield a laser spot pattern at a plurality of optical fibers:
receive one or more voltages; and
electrically steer the light beam with the EO material from a current direction to a next direction in response to the one or more voltages.

2. The system of claim 1, each scanning cell comprising:
a first electrode layer;
an EO element comprising the EO material and disposed outwardly from the first electrode layer; and
a second electrode layer disposed outwardly from the EO element and comprising a set of strip electrodes, a first strip electrode configured to apply a different voltage than a voltage applied by a second strip electrode.

3. The system of claim 1, the EO material comprising a polymer-dispersed liquid crystal (PDLC) material.

4. The system of claim 1, the scanning cell comprising at least two electrodes configured to receive the one or more voltages, each electrode comprising an optically transparent electrically conductive (OTEC) material.

5. The system of claim 1, further comprising:
a controller configured to apply the one or more voltages to yield the spot pattern.

6. The system of claim 1, the number of iterations equal to a number of spots of the pattern.

7. The system of claim 1, the scanning system configured to perform the following for a number of iterations to yield the laser spot pattern by:
directing the light beam to a current laser spot location of the laser spot pattern for a dwell time; and
steering the light beam to a next laser spot location of the laser spot pattern.

8. The system of claim 1, further comprising a controller configured to:
start the light beam substantially when the scanning system is starting to direct the light beam to a current laser spot location of the laser spot pattern for a dwell time; and
stop the light beam substantially when the scanning system is steering the light beam to a next laser spot location of the laser spot pattern.

9. A system comprising:
a housing having an interior region;
one or more lenses disposed within the interior region, each lens configured to transmit a light beam; and
a scanning system disposed within the interior region, the scanning system comprising at least one scanning cell, each scanning cell comprising an electro-optical (EO) material and at least two electrodes, the EO material comprising a polymer-dispersed liquid crystal (PDLC) material, the scanning system configured to perform the following for a number of iterations to yield a laser spot pattern at a plurality of optical fibers:

receive one or more voltages; and
electrically steer the light beam with the ED material from a current direction to a next direction in response to the one or more voltages.

10. The system of claim 9, each scanning cell comprising:
a first electrode layer;
an EO element comprising the ED material and disposed outwardly from the first electrode layer; and
a second electrode layer disposed outwardly from the ED element and comprising a set of strip electrodes, a first strip electrode configured to apply a different voltage than a voltage applied by a second strip electrode.

11. The system of claim 9, further comprising:
a controller configured to apply the one or more voltages to yield the spot pattern.

12. The system of claim 9, the number of iterations equal to a number of spots of the pattern.

13. The system of claim 9, the scanning system configured to perform the following for a number of iterations to yield the laser spot pattern by:
directing the light beam to a current laser spot location of the laser spot pattern for a dwell time; and
steering the light beam to a next laser spot location of the laser spot pattern.

\* \* \* \* \*